(12) United States Patent
Sugita et al.

(10) Patent No.: US 8,445,005 B2
(45) Date of Patent: May 21, 2013

(54) ANTIWRINKLE AGENT, LIPOLYSIS PROMOTER, EXTERNAL COMPOSITION FOR SKIN AND FOOD AND BEVERAGE COMPOSITION

(75) Inventors: Jun Sugita, Kanagawa (JP); Takeshi Ikemoto, Kanagawa (JP); Yumiko Akazawa, Kanagawa (JP); Yurie Kobayashi, Kanagawa (JP); Mitsumasa Mitani, Tokyo (JP); Akinori Haratake, New York, NY (US); Aya Komiya, Kanagawa (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/595,215

(22) Filed: Aug. 27, 2012

(65) Prior Publication Data

US 2012/0322888 A1 Dec. 20, 2012

Related U.S. Application Data

(62) Division of application No. 12/335,326, filed on Dec. 15, 2008, now abandoned, which is a division of application No. 11/661,401, filed as application No. PCT/JP2005/015635 on Aug. 29, 2005, now abandoned.

(30) Foreign Application Priority Data

Aug. 30, 2004 (JP) ................................. 2004-250178
Nov. 5, 2004 (JP) ................................. 2004-321698
Jan. 11, 2005 (JP) ................................. 2005-004506
May 17, 2005 (JP) ................................. 2005-144765
Jun. 16, 2005 (JP) ................................. 2005-176165

(51) Int. Cl.
*A61K 8/02* (2006.01)
*A61K 31/19* (2006.01)
*A61K 31/70* (2006.01)
*A01N 37/10* (2006.01)
*A01N 43/04* (2006.01)

(52) U.S. Cl.
USPC ........................... 424/401; 514/568; 514/25

(58) Field of Classification Search
USPC .......................................................... 424/401
See application file for complete search history.

(56) References Cited

U.S. PATENT DOCUMENTS

| | | | |
|---|---|---|---|
| 4,826,828 A | 5/1989 | Wilmott et al. | |
| 5,834,445 A | 11/1998 | Sikorski et al. | |
| 6,063,381 A | 5/2000 | Staggs | |
| 2002/0115723 A1 | 8/2002 | Iwasaki et al. | |
| 2003/0017997 A1 | 1/2003 | Yokota et al. | |
| 2003/0152682 A1 | 8/2003 | Ley et al. | |
| 2004/0067245 A1 | 4/2004 | Mahalingam et al. | |
| 2005/0260290 A1 | 11/2005 | Raskin et al. | |

FOREIGN PATENT DOCUMENTS

| | | |
|---|---|---|
| JP | 6-239736 A | 8/1994 |
| JP | 10-152404 A | 6/1998 |
| JP | 11-508593 | 7/1999 |
| JP | 2000-169325 A | 6/2000 |
| JP | 3164455 B2 | 3/2001 |
| JP | 2004-107250 A | 4/2004 |
| KR | 1999-025049 A | 4/1999 |
| KR | 2001-0018659 A | 3/2001 |
| WO | WO 92/07586 A1 | 5/1992 |
| WO | WO 2005/065701 A1 | 7/2005 |

OTHER PUBLICATIONS

M.S. Kislalioglu, "Causes, Clinical Features and Management of Skin Aging," Household and Personal Products Industry, vol. 31, No. 5, pp. 61, 62, 64, 66, 68, 70, 72, 74, 76, 78, 80, 82.

Won-Yoon Chung et al., "Antioxidative and antitumor promoting effects of [6]-paradol and its homologs," Mutation Research, 496, 2001, pp. 199-206.

S. N. Park, "Effects of Natural Products on Skin Cells—Action and Suppression of Reactive Oxygen Species," Journal of Korean Cosmetic Association, vol. 25, No. 2, 1999, pp. 77-127.

Nikko Chemicals Co., Ltd., et al., Starting Material for preventing aging (2) antioxidant (Tables 2-3, 2-4), *Cosmetic Handbook*, pp. 456-457, Nov. 1, 1996.

Mitsui, ed., "Anti-oxidation action (Table 1-5)," *New Cosmetology*, published by K.K. Nannzando, pp. 22-23, Jan. 12, 1993.

Ding, "Skin Aging Retardation will still be a Mainstream of Future Cosmetology and Cosmetic Development (Continued)," *Chinese Cosmetic (Industrial Edition)*, pp. 68-75, 2003.

European Search Report issued in application No. 05781045 on Apr. 7, 2011.

(Continued)

*Primary Examiner* — Sreeni Padmanabhan
*Assistant Examiner* — Layla Soroush
(74) *Attorney, Agent, or Firm* — Foley & Lardner LLP

(57) ABSTRACT

An antiwrinkle agent, lipolysis promoter, external composition for skin, and food and beverage composition having for an active ingredient thereof a compound represented by general formula (1):

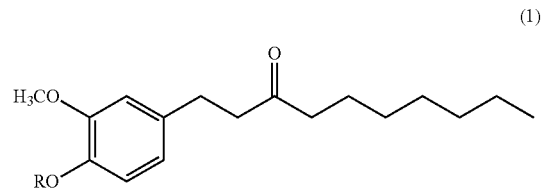

(1)

(wherein R represents a hydrogen atom or an acyl group having 2 to 20 carbon atoms)

or an extract obtained from guinea ginger and/or an acylation treatment product of said extract.

6 Claims, 2 Drawing Sheets

OTHER PUBLICATIONS

Igwilo et al., "Effect of Cream Bases on the Antimicrobial Properties of the Essential Oil of Aframomum meleguata," Int. J. Pharmacognosy, vol. 29, No. 1, pp. 45-50, 1991.

Surh et al., "Anti-Tumor-Promoting Activities of Selected Pungent Phenolic Substances Present in Ginger," Journal of Environmental Pathology, Toxicology and Oncology, vol. 18, No. 2, pp. 131-139, 1999.

Clark et al., "Pungent Compounds: II. Detection and Identification of Paradols (alkyl 4-hydroxy-3-methoxyphenethyl ketones) by Combined Mass Chromotagraphy-Mass Spectrometry," Journal of Chromatography, vol. 134, pp. 315-321, 1977.

Office Action issued by the Examiner in U.S. Appl. No. 12/335,326 on Sep. 16, 2011.

Office Action issued by the Examiner in U.S. Appl. No. 12/335,326 on Oct. 27, 2011.

Office Action issued by the Examiner in U.S. Appl. No. 12/335,326 on May 8, 2012.

Office Action issued by the Examiner in U.S. Appl. No. 11/661,401 on Jan. 22, 2008.

Office Action issued by the Examiner in U.S. Appl. No. 11/661,401 on Sep. 15, 2008.

ANTIWRINKLE AGENT, LIPOLYSIS PROMOTER, EXTERNAL COMPOSITION FOR SKIN AND FOOD AND BEVERAGE COMPOSITION

The present application is a divisional of U.S. application Ser. No. 12/335, 326, filed Dec. 15, 2008 now abandoned, which is a divisional of U.S. application Ser. No. 11/661,401, filed Feb. 28, 2007 now abandoned, which is a U.S. national stage of PCT/JP2005/015635, filed Aug. 29, 2005, which claims priority to Japanese application number 2004-250178, filed Aug. 30, 2004, Japanese application number 2004-321698, filed Nov. 5, 2004, Japanese application number 2005-004506, filed Jan. 11, 2005, Japanese application number 2005-144765, filed May 17, 2005, and Japanese application number 2005-176165, filed Jun. 16, 2005, the entire contents of which are incorporated herein by reference.

TECHNICAL FIELD

The present invention relates to an antiwrinkle agent having superior ameliorative effects on wrinkles occurring with aging, and particularly at sites exposed to sunlight, which maintains the skin in a dermatologically and aesthetically healthy state, and an external composition for skin formulating said antiwrinkle agent.

The present invention also relates to an external composition for skin and food and beverage composition effective for improving an obese constitution by promoting a systemic or local reduction of adipose tissue, or effective for inhibiting or preventing obesity by preventing increases in adipose tissue.

BACKGROUND ART

The organs of all living things, including humans, gradually decline with age following birth and growth, and death occurs when their function stops and portions in which function has stopped exceed a certain degree. This process by which organ function gradually declines is referred to as aging. The skin is subjected directly to the effects of the surrounding environment, and although its function rarely stops completely since it has an important function in maintaining the conditions within the body, it is an organ likely to remarkably show signs of aging such as wrinkles, spots, darkening and sagging, which are particularly prominent at sites exposed to sunlight.

As aging of the skin progresses, the skin's defensive abilities against stimulation by oxidative stress and so forth diminish, and this causes a disturbance of the conditions inside the skin, which in turn further accelerates aging. Since sites exposed to sunlight in particular are continuously exposed to intense oxidative stress caused by irradiation with ultraviolet rays and so forth, the progression of aging is prominent. This progressive change in the skin is referred to as photo-aging, and in skin suffering from photo-aging, collagen, which is a constituting component that accounts for the majority of the dermis, decreases, thereby resulting in an aesthetically undesirable state such as deep, large wrinkles in the surface of the skin.

Although retinoic acid is used as a prescription drug in the US as a substance having ameliorative effects on wrinkles formed as a result of the progression of photo-aging, since it has problems in terms of safety to the occurrence of significant adverse side effects, it has not been approved for use in Japan. In addition, although substances including retinol (vitamin A), which is said to demonstrate effects as a result of being converted to retinoic acid after being absorbed into the body, ascorbic acid (vitamin C), which has antioxidative and collagen synthesis promoting effects, and tocopherol (vitamin E), which has potent antioxidative effects, have also been proposed for use as antiwrinkle agents, these have the shortcoming of being unable to produce sufficiently satisfactory effects. Thus, there has previously not been a substance for use as an antiwrinkle agent capable of demonstrating sufficiently satisfactory effects while also being safe to use.

In addition, many conventional antiwrinkle agents are chemically synthesized, and have numerous problems in terms of safety. On the other hand, with respect to naturally-occurring substances which have few problems in terms of safety, there are hardly any such substances known which can be used as antiwrinkle agents other than vitamins, and what is more, none of them have been obtained which adequately demonstrate ameliorative effects. Moreover, most of natural antiwrinkle agents such as retinol significantly lack photostability, and even if such antiwrinkle agents are effective, nearly all are difficult to formulate into preparations since they are rapidly decomposed in the preparations.

On the other hand, body fat is formed as a result of an excess of ingested energy relative to consumed energy being accumulated in the form of fat in white adipose tissue present around organs and beneath the skin. What is called obesity, in which body fat has accumulated in excess, is not only aesthetically undesirable, but also causes various diseases such as arteriosclerosis, thus making it undesirable in terms of health as well. Recently, there has been an increase in the incidence of obesity caused by such factors as overeating, lack of exercise and stress, and the reduction of body fat or prevention of accumulation thereof is becoming an important issue. In women in particular, there is growing trend towards a preference for a slim, trim physique in terms of appearance.

Capsaicins, which are contained in red peppers and so forth, for example, are known to be substances having obesity preventive action by binding with albumin in the blood and promoting the secretion of hormones from the adrenal glands that promote energy metabolism to activate lipolysis in the liver and adipocytes (see Non-patent document 1). However, since capsaicins exhibit potent stimulation, they have had the problems of limitations on their applications and amounts used.

The present inventors found that raspberry ketone, zingerone and derivatives thereof are effective in inhibiting obesity or improving an obese constitution by promoting the degradation of fat accumulated in adipose tissue (see Patent document 1). However, since raspberry ketone and zingerone have distinctive aroma, they were not necessarily satisfactory with respect to formulated amount and universality.

On the other hand, Guinea ginger (*Aframomum melegueta*), which is a plant of the Zingiberaceae family, is native to tropical regions mainly located in western Africa, and is used as a spice under the name "maniguette" or "grain of paradise". Although Guinea ginger is used as a food seasoning or flavoring, studies have not been conducted on antiwrinkle agents or external compositions for skin using an extract thereof.

Paradol [1-(4'-hydroxy-3'-methoxyphenyl)-3-decanone] has been reported to be a component contained in a specific fraction of a seed extract of the aforementioned guinea ginger, and is a known substance represented by the following chemical formula (see Patent document 2).

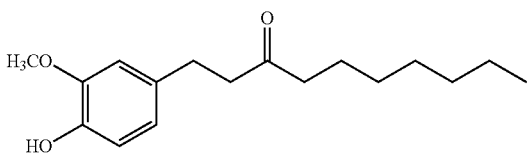 [SMILES: CCCCCCCC(=O)CCc1ccc(O)c(OC)c1]

Although paradol is proposed for use as a termiticide together with other analogs in the Patent document 2, there is no description of wrinkle ameliorative effects, lipolysis promoting effects or slimming effects, and there have been no studies conducted thus far on these effects.

Gingerol and shogaol present in ginger extracts have been proposed for use as active ingredients of promoters of horny layer restoration (see Patent document 3). However, since the paradol in the present invention is a component contained in specific plants of the Zingiberaceae family, and is hardly contained in ordinary ginger, it has not been proposed as an active component of ordinary ginger.

In consideration of the aforementioned circumstances, there has been a need for the development of an antiwrinkle agent and external composition for skin having superior ameliorative effects on wrinkles prominently actualized due to aging, and particularly at sites exposed to sunlight, superior effects in maintaining aesthetically healthy skin, as well as superior safety and stability. In addition, there has also been a need for the development of a lipolysis promoter having effective lipolysis promoting effects while allowing the formulated amount and application to be set as desired without pungent flavor or distinctive aroma, and an external composition for skin and food and beverage composition having superior lipolysis effects while also being superior in terms of characteristics of likeability such as flavor and aroma.

Patent document 1: (Japanese Unexamined Patent Publication No. 2000-169325)
Patent document 2: (Japanese Unexamined Patent Publication No. H10-152404)
Patent document 3: (Japanese Patent No. 3164455)
Non-patent document 1: Iwai, K. and Nakatani, N., ed.: Food Functions of Spice Components, 97, 1989).

As a result of conducting extensive studies in consideration of the aforementioned circumstances, the inventors of the present invention found that guinea ginger (*Aframomum melegueta*), which is a plant of the Zingiberaceae family, and particularly an extract obtained from the seeds thereof as well as an acylation treatment product thereof, along with paradol, which is a component contained in said extract, or an acylation derivative thereof, demonstrate superior ameliorative effects on wrinkles formed with aging, and particularly at sites exposed to sunlight, are effective in maintaining the skin in a dermatologically and aesthetically healthy state, are superior in terms of safety and stability, and are effective in inhibiting or preventing obesity by improving an obese constitution or preventing increases in adipose tissue as a result of promoting reduction of systemic or local adipose tissue, while also being superior materials capable of suppressing pungency and aromas that impair likeability, thereby leading to completion of the present invention.

DISCLOSURE OF THE INVENTION

Namely, the present invention relates to an antiwrinkle agent having for an active ingredient thereof a compound represented by the following general formula (1):

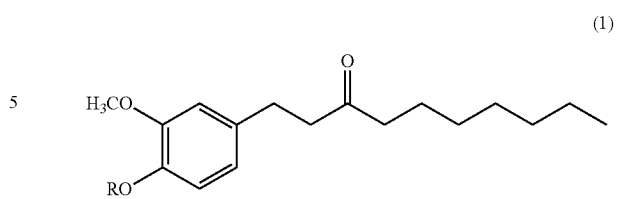

(wherein R represents a hydrogen atom or an acyl group having 2 to 20 carbon atoms)
and an antiwrinkle agent having for an active ingredient thereof an extract obtained from Guinea ginger and/or an acylation treatment product of said extract.

The present invention also relates to a lipolysis promoter having for an active ingredient thereof a compound represented by the aforementioned general formula (1), and a lipolysis promoter having for an active ingredient thereof an extract obtained from guinea ginger and/or an acylation treatment product of said extract.

In addition, the present invention relates to an external composition for skin containing a compound represented by the aforementioned general formula (1), and an external composition for skin containing an extract obtained from guinea ginger and/or an acylation treatment product of said extract.

Moreover, the present invention relates to a food and beverage composition containing a compound represented by the aforementioned general formula (1), and a food and beverage composition containing an extract obtained from guinea ginger and/or an acylation treatment product of said extract.

An antiwrinkle agent and external composition for skin of the present invention demonstrate superior ameliorative effects on wrinkles formed with aging, and particular at sites exposed to sunlight, have effects that maintain the skin in a dermatologically and aesthetically healthy state, and demonstrate superior safety and stability. In addition, a lipolysis promoter, external composition for skin and food and beverage composition of the present invention are effective in improving an obese constitution by promoting reduction of systemic or local adipose tissue or inhibiting or preventing obesity by preventing increases in adipose tissue, and since pungency and aromas that impair likeability are suppressed, in addition to having superior slimming effects, are also considerably superior with respect to feeling at use and likeability. In addition, since the paradol used in the present invention can be easily extracted and purified from a naturally occurring material such as guinea ginger, it enables the obtaining of a composition that is superior in terms of safety as well.

BEST MODE FOR CARRYING OUT THE INVENTION

Figure 1:
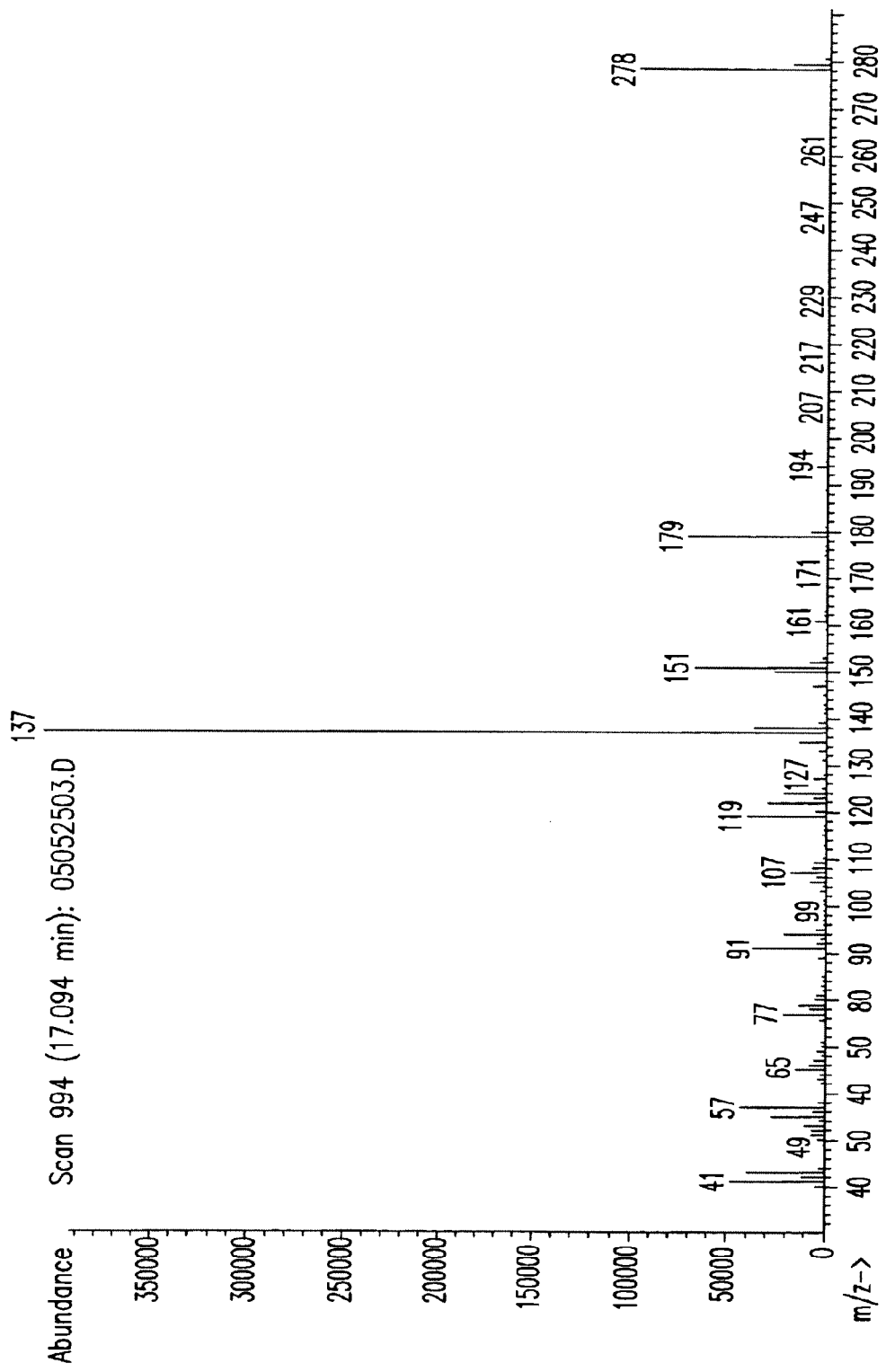
FIG. 1 is a drawing showing the mass spectrum of purified paradol.

The following provides a detailed description of the present invention. The guinea ginger (*Aframomum melegueta*), which is a plant of the Zingiberaceae family, used in the present invention is native to tropical regions located mainly in western Africa, is known under the name "maniguette" or "grain of paradise", and is used as a spice. The extract used in the present invention is an extract able to be obtained from a guinea ginger plant, and particularly the seeds thereof, using known extraction methods. There are no particular limitations on the solvent used for extraction, and examples include lower alcohols or water-containing lower alcohols such as methanol, ethanol, propyl alcohol, isopropyl alcohol and butanol; polyhydric alcohols or water-containing polyhydric alcohols such as 1,3-butylene glycol, or various other types of organic solvents such as acetone, ethyl acetate and hexane.

Although there are no particular limitations on the part of the plant used as an extract material, the seeds are used preferably since the desired extract can be obtained more efficiently.

The resulting extract may be used as is, or it can be made to have a desirable form or properties by subjecting to a procedure such as concentration, drying or dilution as necessary.

In addition, an acylation treatment product of the extract is the result of acylating the extract, and can be obtained from a guinea ginger extract by using an acylation reaction like that described in production process of a compound represented by general formula (1) to be described later.

Paradol [1-(4'-hydroxy-3'-methoxyphenyl)-3-decanone], the compound represented by the aforementioned general formula (1) wherein R is a hydrogen atom, is expressed by the following formula:

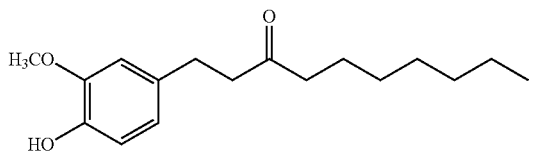

and, as previously described, is a component contained in an extract of guinea ginger. The paradol used in the present invention can be obtained by synthesizing from zingerone using an ordinary organic synthesis method, or by hydrogenating shogaol (Toka Rika Report I, 16, 589, 1927), although there are no particular limitations on the synthesis method.

In addition, paradol can be extracted and purified using a known method by using guinea ginger, and in particular the seeds thereof, as an extraction material. As was previously described, guinea ginger is native to tropical regions located mainly in western Africa, and can be acquired in the form of a spice. Similar to those listed above, examples of extraction solvents that can be used include lower alcohols or water-containing lower alcohols such as methanol, ethanol, propyl alcohol, isopropyl alcohol and butanol; polyhydric alcohols or water-containing polyhydric alcohols such as 1,3-butylene glycol, or various other types of organic solvents such as acetone, ethyl acetate and hexane. A lowly polar solvent such as hexane, heptane or octane is used preferably to increase the paradol concentration in an extract in particular.

Known purification means may be used to purify the paradol from the resulting guinea ginger extract, and for example, paradol can be purified by using silica gel chromatography and so forth.

In a compound represented by the aforementioned general formula (1) in which R represents an acyl group having 2 to 20 carbon atoms, the acyl group having 2 to 20 carbon atoms refers to an R'—CO— group, where R' represents a linear or branched alkyl group having 1 to 19 carbon atoms which may have an unsaturated bond, an aryl group such as phenyl or naphthyl, or a heteroaryl group such as pyridyl, imidazolyl, thienyl or furyl containing a hetero atom selected from a nitrogen atom, sulfur atom and oxygen atom as a ring member. These groups may also have functional groups such as an amino group. Although specific examples of acyl groups having 2 to 20 carbon atoms include acetyl, propionyl, butyryl, isobutyryl, valeryl, hexanoyl, lauroyl, palmitoyl, oleoyl, and the like, acetyl is particularly preferable. Such a compound of formula (1) in which R is an acyl group having 2 to 20 carbon atoms can be synthesized by acylating a phenol compound using a known method. For example, such a compound can be easily obtained by reacting paradol [1-(4'-hydroxy-3'-methoxyphenyl)-3-decanone] obtained according to a method like that described above with an acid chloride or acid anhydride having the desired acyl group in pyridine. Alternatively, paradol can be reacted with a carboxylic acid in the presence of a catalytic amount of base.

Moreover, derivatives of paradol obtained by known methods, such as a glycoside derivative at a hydroxyl group at the 4-position of the aromatic ring or a derivative resulting from reducing the ketone group, are treated as being equivalent to paradol and can be used in the present invention.

In the present invention, a compound represented by the aforementioned general formula (1), and an extract obtained from guinea ginger, and particularly from the seeds thereof, and/or an acylation treatment product of said extract can be used as an antiwrinkle agent. In the case of using an extract, the extract can be used as such, or it can be made to have a desirable form or properties by subjecting to a procedure such as concentration, drying or dilution as necessary.

In the present invention, in the case of formulating a compound represented by the aforementioned general formula (1), and an extract obtained from guinea ginger, and particularly from the seeds thereof, and/or an acylation treatment product of said extract into an external composition for skin as an antiwrinkle agent, the formulated amount thereof in terms of paradol is preferably 0.001 to 10.0% by mass (hereinafter simply abbreviated as %), particularly preferably 0.01 to 8.0%, more preferably 0.05 to 5% and most preferably 0.1 to 3% based on the total weight of the external composition for skin. If the formulated amount is less than 0.001%, the desired effects of the present invention are inadequate, while even if the formulated amount exceeds 10.0%, an increase in effects corresponding to that increase is not observed, thereby making this undesirable.

In addition, in the case of formulating the compound or the like described above into an external composition for skin as an antiwrinkle agent, combining with the use of conventional components known to have wrinkle ameliorative effects such as retinol, ascorbic acid and tocopherol is preferable since these components enable the realization of complementary or synergistic wrinkle ameliorative effects.

In the present invention, a compound represented by the aforementioned general formula (1), and an extract obtained from guinea ginger, and particularly from the seeds thereof, and/or an acylation treatment product of said extract can be formulated into an external composition for skin or food and beverage composition as a lipolysis promoter that promotes lipolysis.

In the case of formulating a compound represented by the aforementioned general formula (1), and an extract obtained from guinea ginger, and particularly from the seeds thereof, and/or an acylation treatment product of said extract into an external composition for skin and food and beverage composition as a lipolysis promoter, although unable to be uniformly defined as a result of varying according to the preparation form, the formulated amount in terms of paradol is preferably, for example, 0.001 to 10.0% by mass (hereinafter simply abbreviated as %), particularly preferably 0.01 to 8.0%, more preferably 0.05 to 5% and most preferably 0.1 to 3% based on the total weight of said composition. If the formulated amount is less than 0.001% by mass, the effects of the invention may not be demonstrated, while if the formulated amount exceeds 10% by weight, pungency increases which may result in impairment of sensory characteristics and likeability. In addition, the amount consumed by an adult of the food and beverage composition is 20 to 1000 mg, and preferably 100 to 200 mg, in terms of paradol.

In addition, other components having obesity inhibitory or preventive action such as raspberry ketone, zingerone, 4-(3', 4'-dihydroxyphenyl)-2-butanone or synephrine may be suitably combined and formulated into an external composition for skin or food and beverage composition used as a lipolysis promoter of the present invention for the purpose of increasing or reinforcing the effects thereof.

In addition, stimulants of β-adrenalin action such as butopamine and isoproterenol, inhibitors of α2-adrenalin action such as yohimbine and ergotoxin, xanthin derivatives such as theophylline and caffeine, or bipyridine derivatives such as milrinone and amrinone can also be formulated into an external composition for skin or food and beverage composition used as a lipolysis promoter of the present invention.

Moreover, various other ordinarily used components can also be formulated as necessary into an external composition for skin or food and beverage composition of the present invention within a range that does not impair the effects thereof. Examples of components that can be formulated into an external composition for skin include components ordinarily formulated into external compositions such as oils, pigments, fragrances, surfactants, moisture retainers, ultraviolet absorbers, anti-inflammatory agents, bacteriocides, dyes, preservatives, and antioxidants, while examples of components that can be formulated into food and beverage compositions include components such as vehicles, binders, thickeners, emulsifiers, colorants, fragrances, food additives, and flavorings.

An external composition for skin of the present invention corresponds to not only a skin cosmetic, but also a pharmaceutical or bath additive. Although there are no particular limitations on the form, in the case of an external composition for skin, examples of forms include skin toners (lotions), skin creams, bathing creams and washing creams, milky lotions, gels, packs, sticks, sheets, adhesive skin patches, powders, liquids and granules. In the case of a food and beverage composition, examples of forms include tablets, hard candies, pills, sugar-coated tablets, powders, granules, leaves, tea bags, hard capsules, soft capsules, chewing gum, chocolate, candies, jellied candies, beverages, soups, ice cream, noodles and bakery products.

EXAMPLES

The following provides a detailed explanation of the present invention based on Examples and Comparative examples thereof, but the present invention is not limited to these examples. Furthermore, unless specifically indicated otherwise, "%" in Examples refers to "% by mass".

Production Example 1

Production of Guinea Ginger Extract

After crushing 2 g of dried guinea ginger (*Aframomum melequeta*) seeds with a mixer, the crushed seeds were extracted by immersing in 20 ml of acetone for 24 hours. The resulting extract was concentrated and dried under reduced pressure to obtain 0.1 g of an extract from guinea ginger seeds. This extract is referred to as "guinea ginger extract". According to the results of HPLC analysis, this guinea ginger extract contained 55% paradol.

Production Example 2

Production of Paradol

After crushing 100 g of dried guinea ginger (*Aframomum melegueta*) seeds with a mixer, the crushed seeds were immersed in 2 liters of hexane for 24 hours. The resulting extract was concentrated and dried under reduced pressure to obtain 2.0 g of extract. This extract was fractionated by silica gel chromatography (hexane/ethyl acetate (9:1)) using Silica Gel 60N (100 to 210 μm, Kanto Chemical) to obtain about 500 mg of purified paradol.

(Identification of Paradol)

The purified paradol was confirmed by GC-MS and $^{13}$C-NMR (100 MHz, CDCl$_3$). Those results are shown below.

Figure 2:
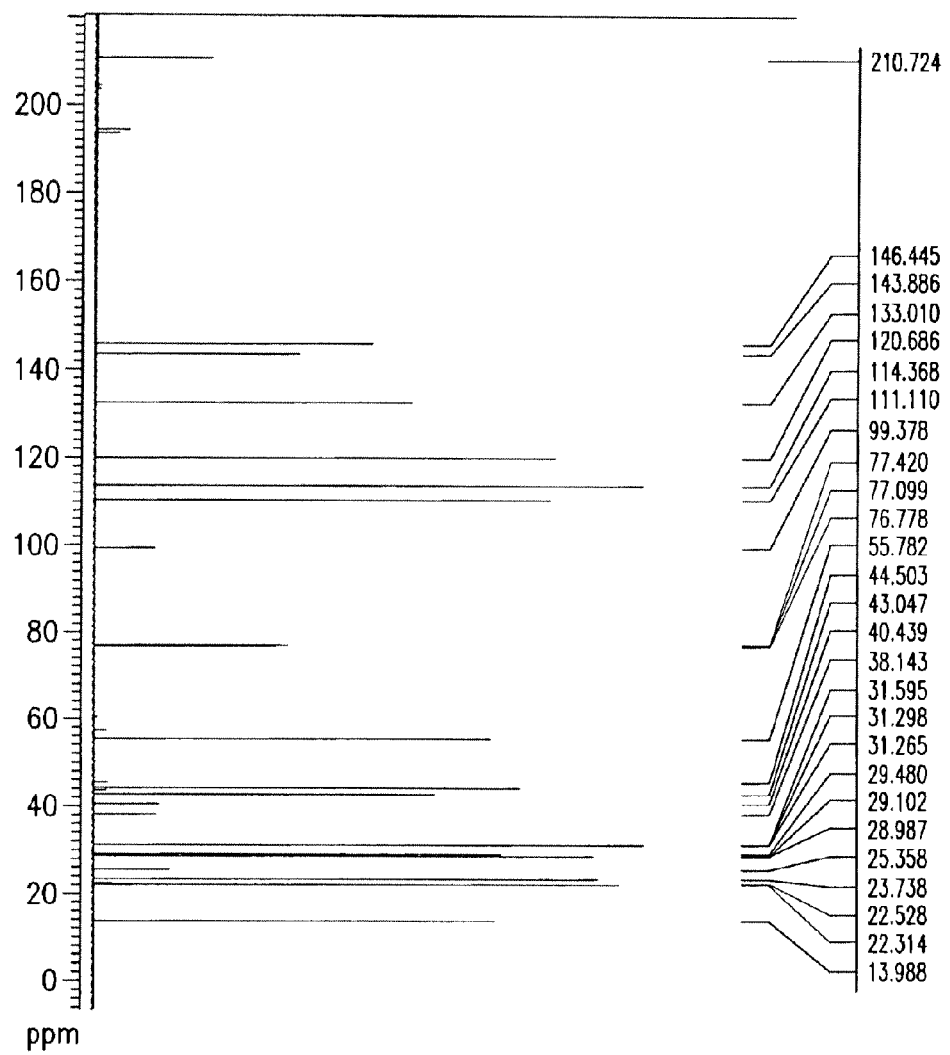
FIG. 2 is a drawing showing the $^{13}$C-NMR spectrum (100 MHz, CDCl$_3$) of purified paradol.

Molecular ion peak (M$^+$) (m/z: 278) was detected by GC-MS (see FIG. 1). The following signals were detected by $^{13}$C-NMR [δ (ppm): 14.0, 22.5, 23.7, 29.1, 29.4, 31.2, 43.0, 44.5, 55.7, 111.1, 114.3, 120.6, 133.0, 143.8, 146.4, 210.7] (see FIG. 2).

Production Example 3

Production of Acetylated Guinea Ginger Extract 1.0 g of the guinea ginger extract obtained in Production Example 1, 1.0 ml of pyridine and 30 ml of acetic anhydride were mixed and stirred at room temperature for 24 hours. Then, after water was added thereto, the mixture was extracted with ethyl acetate to obtain 1.2 g of acetylation treatment extract. This treated product was referred to as "acetylated guinea ginger extract".

Production Example 4

Production of Paradol 10 g (6.5 mmol) of vanillin and 9.3 g (6.5 mmol) of 2-nonanone were dissolved by stirring in 30 ml of hexane and 20 ml of diethyl ether. Moreover, after adding 3.9 g of acetic acid, 4.6 ml (6.5 mmol) of piperidine was added followed by stirring for 6 hours. Following completion of the reaction, unreacted vanillin was removed with an aqueous sodium bicarbonate solution followed by extraction with diethyl ether. After drying with anhydrous magnesium sulfate, the solvent was distilled off to obtain 20.2 g of crude product. The crude product was purified by column chromatography (SiO$_2$/CHCl$_3$) to obtain (E)-1-(4'-hydroxy-3'-methoxyphenyl)dec-1-en-3-one (17.94 g, yield: 90%).

Moreover, 10 g (36 mmol) of the resulting (E)-1-(4'-hydroxy-3'-methoxyphenyl)dec-1-en-3-one was dissolved in 100 mL of ethanol followed by the addition of 1 g of palladium carbon (5% palladium) to this solution and stirring overnight at normal temperature in a hydrogen atmosphere (normal pressure). After filtering the insoluble matter, the filtrate was concentrated under reduced pressure to obtain 9.8 g of crude product. This crude product was purified by column chromatography (SiO$_2$/CHCl$_3$) to obtain 1-(4'-hydroxy-3'-methoxyphenyl)-3-decanone (5.6 g, yield: 58%).

Examples 1-3

Wrinkle Ameliorative Effects of Guinea Ginger Extract, Paradol and Acetylated Guinea Ginger Extract Samples containing 1.0% each of the guinea ginger extract, paradol or acetylated guinea ginger extract obtained in Production Examples 1 to 3 were prepared, using a 50% aqueous ethanol solution for the base (Example 1, 2 or 3, respectively), and wrinkle ameliorative effects on photoaged skin were investigated using the test method described below.

(Test Method)

1. Test Animals

Hairless mice, 10 weeks old at the start of the test, were used in groups of 10 animals each.

2. Evaluation of Wrinkle Ameliorative Effects 2-1. Photo-Aging Conditions

Photo-aging was induced by irradiating skin with UVA and UVB once a day, five times a week for eight weeks. The irradiated doses were 20, 25 and 30 J/cm$^2$ for UVA and 20, 30 and 40 mJ/cm$^2$ for UVB. The doses were elevated every week, and the skin was irradiated at the maximum doses after the third week.

2-2. Evaluation Method

Wrinkle ameliorative effect was evaluated using a wrinkle score and a dermal collagen level. The wrinkle score was determined according to the method of Bissett, et al. (Photochem. Photobiol., 46: 367-378, 1987). Namely, the size and depth of wrinkles were comprehensively evaluated macroscopically, and evaluated according to one of four levels consisting of a score of 3 for "large, deep wrinkles able to be confirmed", 2 for "wrinkles able to be confirmed", 1 for "wrinkles unable to be confirmed" and 0 for "normal skin texture observed". The dermal collagen level was evaluated by sampling whole layer of the skin and homogenizing with a Polytron Homogenizer (Kinematica), followed by extraction and acid-hydrolysis of the collagen fraction, and finally quantifying the hydroxyproline content using amino acid analyzer (Jasco). The amount of hydroxyproline per 1 cm$^2$ was used as a relative indicator of dermal collagen level.

3. Test Procedure

Samples were prepared by formulating guinea ginger extract (Production Example 1), paradol (Production Example 2) or acetylated guinea ginger extract (Production Example 3) at 1.0% each (0.55% or 0.8% as the concentration of paradol, 0.5% as the concentration of acetyl paradol) using a 50% aqueous ethanol solution for the base (Example 1, 2 or 3). Furthermore, the base solution was used as a comparative example. These evaluation samples were applied in an amount of 0.1 ml at a frequency of once a day, five times a week to dorsal skin of the hairless mice (diameter: about 2.5 cm) from the 5th week after the start of UV irradiation until the 4th week following completion of irradiation. Wrinkle scores were then determined following completion of the final application. After the animals were sacrificed, skin samples were obtained followed by measurement of collagen content (amount of hydroxyproline per 1 cm$^2$).

(Test Results)

Wrinkle ameliorative effects for Examples 1 to 3 are shown below in terms of the evaluation results of wrinkle scores and dermal collagen levels.

(Wrinkle Score Evaluation Results 1)

| Group | Wrinkle Score (mean ± SE) |
|---|---|
| Example 1 (guinea ginger extract) | 2.45 ± 0.09 |
| Example 2 (paradol) | 2.40 ± 0.23 |
| Comparative Example 1 (base only) | 2.65 ± 0.08 |

(Wrinkle Score Evaluation Results 2)

| Group | Wrinkle Score (mean ± SE) |
|---|---|
| Example 3 (acetylated guinea ginger extract) | 2.55 ± 0.09 |
| Comparative Example 2 (base only) | 2.75 ± 0.09 |

The antiwrinkle agent application groups of Examples 1 to 3 in which guinea ginger extract, paradol or acetylated guinea ginger extract was used for the active ingredient demonstrated lower wrinkle scores than the base only application group of Comparative Example 1 or 2, thereby indicating that an antiwrinkle agent of the present invention is effective.

(Collagen Content Evaluation Results)

| Group | Hydroxyproline level (mean ± SE) ($\mu$mol/cm$^2$) |
|---|---|
| Example 1 (guinea ginger extract) | 6.49 ± 0.41 |
| Comparative Example 1 (base only) | 5.64 ± 0.35 |

The antiwrinkle agent application group in which the guinea ginger extract of Example 1 was used as an active ingredient demonstrated a higher collagen content (amount of hydroxyproline) than the base only application group of Comparative Example 1, thereby indicating that an antiwrinkle agent of the present invention is effective against reductions in dermal collagen levels caused by photo-aging.

On the basis of the above test results, an antiwrinkle agent of the present invention having for an active ingredient thereof the guinea ginger extract, paradol or acetylated guinea ginger extract of Examples 1 to 3 is clearly effective in improving wrinkles caused by photo-aging.

In addition, similar effects were obtained when testing was carried out in the same manner using the paradol obtained in Production Example 4 instead of the paradol obtained in Production Example 2.

Example 4

Evaluation of Pungent Flavor

A sensory evaluation of the paradol, extracted and purified in Production Example 2, was made in terms of the spicy flavor. Capsaicin, which is a pungent component of red peppers, was used as a comparative subject. The paradol and capsaicin were diluted with distilled water to prepare test liquids having concentrations of $10^{-8}$ mol/L to $10^{-3}$ mol/L. Sensory evaluations were conducted on the test liquids in the order starting from the lowest concentration, and the concentration at which pungent flavor is perceived was designated as the threshold value. As can be understood from the following results, while the threshold value of capsaicin was about $10^{-7}$ mol/L, that of paradol was $10^{-4}$ mol/L, and thus the spicy flavor of paradol was found to be weak, equivalent to only about 1/1000 that of capsaicin. This result indicates that a food and beverage composition of the present invention is suitable for foods and beverages.

|  | Evaluated Concentration (mol/L) | | | | | |
| --- | --- | --- | --- | --- | --- | --- |
|  | $10^{-3}$ | $10^{-4}$ | $10^{-5}$ | $10^{-6}$ | $10^{-7}$ | $10^{-8}$ |
| Capsaicin | +++ | ++ | + | ± | ± | − |
| Paradol | + | ± | − | − | − | − |

Legend:
+++ Extremely potent spicy flavor
++ Very spicy flavor
+ Somewhat spicy flavor
± Slight spicy flavor
− No spicy flavor Moreover, similar results were obtained when the test was carried out in the same manner as described above using the paradol produced in Production Example 4 instead of the paradol obtained in Production Example 2.

Example 5

Lipolysis Promoting Effects (Test Method)
Mouse 3T3-L1 cells purchased from Dainippon Pharmaceutical Co., Ltd. were cultured in a 24-well culture plate according to the method of Ensler, et al. (Ensler, K. et al., Biochim. Biophys. Acta., 1581: 36-48 (2002)) at 37° C. in a 5% (v/v) $CO_2$ atmosphere, and these cells were used in the test as mature adipocytes. Test media were prepared by adding test samples at predetermined concentrations to DMEM medium containing bovine serum albumin and norepinephrine (final concentration: $3 \times 10^{-8}$ mol/L). The said mature adipocytes were cultured in the test media for 90 minutes to be reacted with the test samples. Following the reaction, the glycerol released into the media was quantified by enzyme immunoassay using the F Kit Glycerol (Roche).

The lipolysis promotion rate was calculated according to the equation below based on the quantified glycerol values to serve as an indicator of lipolysis promoting effect:

Lipolysis promotion rate(%)=$[A/B] \times 100$ (wherein A represents the amount of glycerol with addition of test sample, and B represents the amount of glycerol of a control (without addition of test sample)).
(Test Results)
The results of evaluating the lipolysis promoting effects of the guinea ginger extract and paradol produced in Production Examples 1 and 2 using the lipolysis test described above are shown below. Zingerone and caffeine were used as comparative controls.

| Test sample | Test concentration (% by mass) | Lipolysis promotion rate (%) (mean ± SE) | Statistical difference (versus control) |
| --- | --- | --- | --- |
| Guinea ginger extract | 0.01 | 119.40 ± 14.03 | −(n.s.) |
|  | 0.10 | 383.45 ± 35.12 | +(p < 0.001) |
| Paradol | 0.10 | 554.68 ± 107.62 | +(p < 0.001) |
| Zingerone | 0.10 | 191.85 ± 69.83 |  |
| Caffeine | 0.10 | 234.93 ± 11.23 | +(p < 0.05) |

The lipolysis promotion rates of the guinea ginger extract obtained in Production Example 1 and the paradol obtained in Production Example 2 were much higher than that of zingerone and caffeine used as comparative examples, thereby clearly demonstrating that guinea ginger extract and paradol have potent lipolysis promoting action.

In addition, similar results were obtained when the test was carried out in the same manner using the paradol obtained in Production Example 4 instead of the paradol obtained in Production Example 2.

Example 6

Weight Gain Inhibition Test (Test Method)
ICR mice (males, age 4 weeks) were used in the test in two groups of six animals each. To the control group, a high fat diet having the composition indicated below was given for six weeks, while to the test group, a high fat diet containing 1% by mass of the guinea ginger extract obtained in Production Example 1 was given. The body weights of the animals were measured at the start of the test and in the 6th week after the start of the test, and differences between the groups were evaluated based on body weight gain to assess weight gain inhibitory effects. The animals were given free access to food and water.
(Composition of High Fat Diet)

| Ingredient | Formulated Amount (% by mass) |
| --- | --- |
| Beef tallow | 40 |
| Cornstarch | 10 |
| Granulated sugar | 9 |
| Minerals*1 | 4 |
| Vitamins*2 | 1 |
| Casein | Remainder |

*1: Mineral Mix (ICN)
*2: Vitamin Mix (ICN)

(Test Results)
The results are shown below.

| Group | Weight gain (g) (mean ± SE) | Statistical difference (versus control group) |
| --- | --- | --- |
| Control group | 26.4 ± 5.3 |  |
| Test group | 14.9 ± 1.5 | +(p < 0.05) |

As is clear from the above results, weight gain resulting from ingestion of a high fat diet was shown to decrease significantly as a result of formulating guinea ginger extract, a lipolysis promoter of the present invention, into a high fat diet.

In the present invention, various types of external skin preparations and food and beverage compositions can be provided by formulating therein a compound represented by general formula (1), guinea ginger, particularly an extract obtained from seeds thereof and/or an acylation treatment product of said extract. The following indicates examples thereof, but the present invention is not limited to these examples.

Examples 7, 8 and Comparative Example 3

Skin Lotion

Skin lotions having the compositions indicated below were prepared according to ordinary methods followed by evaluation of wrinkle ameliorative effects according to the following procedure using these skin lotions as samples. The test subjects consisted of healthy persons having wrinkles in the outer corners of their eyes (women, age 41 to 65, of which 10 women each were used in Example 7 or Example 8). The skin lotion of Example 7 or 8 was applied, in an aliquot of roughly 0.2 ml, to wrinkles in the outer corner of either eye, while the skin lotion of Comparative Example 3 to wrinkles of the other eye (over an area measuring about 2×2 cm, or about 4 cm², centering around the wrinkles), twice a day after washing the face in the morning and after bathing at night, for two consecutive months (60 days). The subjects were then asked to fill out a questionnaire relating to the conditions of the skin (wrinkles) in both the corners of the eyes following the final application.

(Composition)

| | Formulated Amount (%) | | |
|---|---|---|---|
| Raw Ingredient | Example 7 | Example 8 | Comparative Example 3 |
| (1) Butylene glycol | 30.0 | 30.0 | 30.0 |
| (2) Polyoxyethylene (20) sorbitan monolaurate | 0.5 | 0.5 | 0.5 |
| (3) Propylene glycol | 20.0 | 20.0 | 20.0 |
| (4) Glycerin | 10.0 | 10.0 | 10.0 |
| (5) Methyl paraben | 0.1 | 0.1 | 0.1 |
| (6) Ethanol | 7.0 | 7.0 | 7.0 |
| (7) Guinea ginger extract (Production Example 1) | 1.0 | — | — |
| (8) Paradol (Production Example 2) | — | 1.0 | — |
| (9) Purified water | Remainder | Remainder | Remainder |

On the basis of the results of the questionnaires, the numbers of subjects who indicated that the skin lotion of Example 7 or Example 8 is more effective than that of Comparative Example 3 for each of the evaluation parameters relating to skin condition (wrinkles) are shown below.

| Evaluation Parameter | Example 7 (No. of subjects) | Example 8 (No. of subjects) |
|---|---|---|
| Wrinkles became inconspicuous | 5 | 3 |
| Skin became softer | 4 | 3 |
| Skin became turgor | 5 | 4 |
| Skin had more luster | 3 | 5 |
| Skin became brighter | 4 | 3 |

According to the results of this test, the skin lotions of Examples 7 and 8 clearly improved wrinkles as compared with the skin lotion of Comparative Example 3, while also improving poor skin flexibility and color tone caused by photo-aging. In addition, there was no skin abnormalities including irritation and itching observed to have been caused by the skin lotions of the present invention.

In addition, similar results were obtained when the test was carried out in the same manner using the paradol obtained in Production Example 4 instead of the paradol obtained in Production Example 2.

Example 9

Skin Cream

Skin creams formulating guinea ginger extract and paradol or acetylated guinea ginger extract according to the compositions indicated below were prepared according to ordinary methods. Twenty healthy persons (women age 50 to 55), who were found to be concerned about wrinkles in the corners of the eyes in a preliminary survey, used about 0.5 g of the skin creams once a day for one week or longer, followed by a questionnaire survey.

(Composition)

| Raw Ingredient | Formulated Amount (%) |
|---|---|
| (1) Beeswax | 2.0 |
| (2) Stearic acid | 5.0 |
| (3) Stearyl alcohol | 5.0 |
| (4) Hydrogenated lanolin | 2.0 |
| (5) Squalene | 20.0 |
| (6) Sorbitan monostearate | 3.0 |
| (7) Polyoxyethylene (20) sorbitan monostearate | 3.0 |
| (8) Propylene glycol | 5.0 |
| (9) Methyl paraben | 0.2 |
| (10) Purified water | Remainder |
| (11) Guinea ginger extract (Production Example 1) | 1.0 |
| (12) Paradol (Production Example 2) or acetylated guinea ginger extract (Production Example 3) | 1.0 |

The results of the questionnaire survey are shown below. The results indicate the numbers of subjects who responded as indicated after use as compared with before use for each parameter.

| Evaluation Parameter | No. of Subjects |
|---|---|
| Wrinkles became inconspicuous | 15 |
| Wrinkle size decreased | 16 |
| Number of wrinkles decreased | 7 |
| Wrinkles increased | 0 |

According to the results of this test, in the case of the skin cream of Example 9, nearly all of the subjects indicated that they felt that wrinkles became less conspicuous after use as compared with before use, and that improvement of wrinkles caused by photo-aging was the result of decreasing the size of wrinkles rather than the number of wrinkles as the cause thereof. In addition, there was no skin abnormalities including irritation and itching observed to have been caused by the skin cream of the present invention.

In addition, similar results were obtained when the test was carried out in the same manner using the paradol obtained in Production Example 4 instead of the paradol obtained in Production Example 2.

Examples 10 and 11 and Comparative Examples 4 to 7

Chewing Gum

Chewing gum having the compositions indicated below were produced. The resulting gum was ingested (15 g/day) for one month by women in their twenties having the percentage of body fat of 35% or more in groups of 30 women each followed by an evaluation by designating those subjects whose percentage of body fat had decreased by 5% or more of their originals' as subjects demonstrating reduced body fat.

|  | Formulated Amount (% by mass) | | |
| --- | --- | --- | --- |
| Ingredient | Example 10 | Comparative Example 4 | Comparative Example 5 |
| (1) Gum base | 20 | 20 | 20 |
| (2) Maltitol | 73.5 | 74.5 | 70.5 |
| (3) Hydrogenated malt syrup | 4 | 4 | 4 |
| (4) Apple flavoring | 0.5 | 0.5 | 0.5 |
| (5) Yucca extract*[1] | 1 | 1 | 5 |
| (6) Guinea ginger extract (Production Example 1) | 1 | — | — |
| Evaluation: No. of subjects demonstrating reduced body fat | 24 | 9 | 21 |

|  | Formulated Amount (% by mass) | | |
| --- | --- | --- | --- |
| Ingredient | Example 11 | Comparative Example 6 | Comparative Example 7 |
| (1) Gum base | 20 | 20 | 20 |
| (2) Maltitol | 73.5 | 74.5 | 70.5 |
| (3) Hydrogenated malt syrup | 4 | 4 | 4 |
| (4) Apple flavoring | 0.5 | 0.5 | 0.5 |
| (5) Yucca extract*[1] | 1 | 1 | 5 |
| (6) Paradol (Production Example 2) | 1 | — | — |
| Evaluation: No. of subjects demonstrating reduced body fat | 24 | 10 | 15 |

*[1] "Yucca Saponin 50M" (Tokiwa Phytochemical) (containing 45 to 50% by mass saponin)

In addition, similar results were obtained when the test was carried out in the same manner using the paradol obtained in Production Example 4 instead of the paradol obtained in Production Example 2.

Example 12

Hard Candy

Hard candies (0.5 g/candy) were produced having the compositions indicated below, and were ingested by subjects (three candies per day), followed by evaluation under the same conditions as Examples 10 and 11 above.

| Ingredient | Formulated Amount (% by mass) |
| --- | --- |
| (1) Sorbitol | 85.9 |
| (2) Sucrose fatty acid ester | 6 |
| (3) Raspberry flavoring | 0.1 |
| (4) Yucca extract*[1] | 3 |
| (5) Guinea ginger extract (Production Example 1) | 5 |
| Evaluation: No. of subjects demonstrating reduced body fat | 26 |

| Ingredient | Formulated Amount (% by mass) |
| --- | --- |
| (1) Sorbitol | 85.9 |
| (2) Sucrose fatty acid ester | 6 |
| (3) Raspberry flavoring | 0.1 |
| (4) Yucca extract*[1] | 3 |
| (5) Paradol (Production Example 2) | 5 |
| Evaluation: No. of subjects demonstrating reduced body fat | 23 |

*[1] "Yucca Saponin 50M" (Tokiwa Phytochemical) (containing 45 to 50% by mass saponin)

As is clear from the above evaluation results, the food and beverage compositions (chewing gum and hard candy) of the aforementioned examples demonstrated remarkable percentage of body fat-lowering action. Moreover, a food and beverage composition of the present invention is ingested easily, has superior likeability, and is suitable for continuous ingestion because of its retention of appeal even after ingestion for a long period of time.

In addition, similar effects were obtained when the test was carried out in the same manner using the paradol obtained in Production Example 4 instead of the paradol obtained in Production Example 2.

Examples 13 and 14 and Comparative Examples 8 and 9

Gel-Like Slimming Skin Cosmetic

Components A and B having the compositions indicated below were individually mixed and dissolved in accordance with ordinary methods followed by the addition of Component B to Component A and stirring to prepare gel-like slimming skin cosmetics.

|  | Formulated Amount (% by mass) | |
| --- | --- | --- |
| Ingredient | Example 13 | Comparative Example 8 |
| Component A | | |
| (1) Guinea ginger extract (Production Example 1) | 3.0 | — |
| (2) Glycerin | 10.0 | 10.0 |
| (3) Carboxyvinyl polymer | 0.3 | 0.3 |
| (4) Disodium edetate | 0.1 | 0.1 |
| (5) Purified water | Remainder | Remainder |
| (6) Diisopropanol amine | 1.0 | 1.0 |
| (7) Squalane | 10.0 | 10.0 |
| Component B | | |
| (8) Polyoxyethylene (60) hydrogenated castor oil | 0.8 | 0.8 |
| (9) Carrageenan | 3.0 | 3.0 |
| (10) Xanthane gum | 3.0 | 3.0 |
| (11) Polyvinyl alcohol | 2.0 | 2.0 |
| (12) Ethanol | 45.0 | 45.0 |
| (13) Menthol | 0.1 | 0.1 |
| (14) Fragrance | q.s. | q.s. |
| Evaluation: Slimming effect (no. of subjects) | 16 | 5 |

| Ingredient | Formulated Amount (% by mass) | |
| --- | --- | --- |
| | Example 14 | Comparative Example 9 |
| Component A | | |
| (1) Paradol (Production Example 2) | 3.0 | — |
| (2) Glycerin | 10.0 | 10.0 |
| (3) Carboxyvinyl polymer | 0.3 | 0.3 |
| (4) Disodium edetate | 0.1 | 0.1 |
| (5) Purified water | Remainder | Remainder |
| (6) Diisopropanol amine | 1.0 | 1.0 |
| (7) Squalane | 10.0 | 10.0 |
| Component B | | |
| (8) Polyoxyethylene (60) hydrogenated castor oil | 0.8 | 0.8 |
| (9) Carrageenan | 3.0 | 3.0 |
| (10) Xanthane gum | 3.0 | 3.0 |
| (11) Polyvinyl alcohol | 2.0 | 2.0 |
| (12) Ethanol | 45.0 | 45.0 |
| (13) Menthol | 0.1 | 0.1 |
| (14) Fragrance | q.s. | q.s. |
| Evaluation: Slimming effect (no. of subjects) | 14 | 3 |

The above gel-like slimming skin cosmetics were applied in aliquots of about 2 g twice a day for three consecutive weeks to the abdomen and thighs of 20 subject panelists each followed by a questionnaire survey of their slimming effects. As indicated by the evaluation results above, the number of subjects who responded that their abdomen and thighs had become slimmer as compared with prior to application was much larger among panelists using a gel-like slimming skin cosmetic of the present invention. In addition, there were no particular problems with a gel-like slimming skin cosmetic of the present invention with respect to likeability such as fragrance and irritation and so forth during use.

Similar effects were observed when the test was carried out in the same manner using the paradol obtained in Production Example 4 instead of the paradol obtained in Production Example 2.

The compositions of the fragrances used in the present example are shown in Table 1 below.

TABLE 1

| Fragrance Formula | |
| --- | --- |
| Ingredient | % by mass |
| Terpineol | 10.00 |
| Terpinyl acetate | 2.00 |
| Sepionate | 60.00 |
| Methyldihydrojasmonate | 250.00 |
| Indole | 0.05 |
| 2-Methyl-3-(3,4-methylenedioxy-phenyl)-propanal | 3.00 |
| Hydroxycitronellal | 20.00 |
| Hydroxycitronellol | 10.00 |
| p-t-Butyl-α-methylhydroxy cinnamic aldehyde | 35.00 |
| 4-(4-Hydroxy-4-methyl-pentyl)-3-cyclohexene-1-carboxy-aldehyde | 75.00 |
| 3-Methyl-5-phenylpentanol | 20.00 |
| Phenyl ethyl alcohol | 10.00 |
| α-ionone | 10.00 |
| β-ionone | 20.00 |
| γ-methylionone | 10.00 |
| Dihydro-β-ionone | 25.00 |
| Benzyl salicylate | 150.00 |
| Cis-3-hexenyl salicylate | 30.00 |
| Eugenol | 0.80 |
| Cinnamic alcohol | 5.00 |
| Cinnamic aldehyde | 0.50 |
| Guaiol acetate | 1.00 |
| Guaiol | 0.50 |
| Cedrenyl acetate | 5.00 |
| Cedryl methyl ketone | 30.00 |
| 6,7-Dihydro-1,1,2,3,3-pentamethyl-4(5H)-indan | 2.00 |
| Vetiver acetate | 10.00 |
| 3-Methyl-5-(2,3,3-trimethyl-3-cyclopenten-1-yl)-pentan-2-ol | 2.00 |
| 2-Ethyl-4-(2,3,3-trimethyl-3-cyclopenten-1-yl)-2-buten-1-ol | 0.80 |
| Isobornyl cyclohexanol | 35.00 |
| Heliotropin | 10.00 |
| Coumarin | 2.00 |
| Vanillin | 2.00 |
| Ethyl vanillin | 0.10 |
| Muscone | 0.50 |
| Ethylene brassylate | 42.00 |
| 4,6,6,7,8,8-Hexamethyl-1,3,4,6,7,8-hexahydro-cyclopentabenzopyrane | 60.00 |
| Cyclopentadecanolide | 20.00 |
| Ambrettolide | 1.00 |
| γ-undecalactone | 0.40 |
| γ-decalactone | 0.10 |
| 4-(4-Hydroxyphenyl)-2-butanone | 0.50 |
| Musk ketone | 0.10 |
| Skatole | 0.01 |
| Cis-jasmone | 0.05 |
| Phenylethyl acetate | 0.10 |
| Civetone | 0.20 |
| γ-nonalactone | 0.05 |
| α-santalol | 0.20 |
| β-santalol | 0.20 |
| Eugenyl acetate | 0.10 |
| α-hexylcinnamic aldehyde | 20.00 |
| α-damascone | 0.04 |
| β-damascone | 0.02 |
| β-damasenone | 0.01 |
| δ-damascone | 0.01 |
| Rose absolute | 0.50 |
| Rose oil | 4.50 |
| Sandalwood oil | 2.00 |
| Labdanum absolute | 0.05 |
| Ciste absolute | 0.01 |
| Vetiver oil | 0.50 |
| Guaiac wood oil | 0.10 |
| Total | 1000.00 |

INDUSTRIAL APPLICABILITY

According to the present invention, an antiwrinkle agent having superior ameliorative effects on wrinkles occurring with aging, and particularly at sites exposed to sunlight, having effects that maintain the skin in a dermatologically and aesthetically healthy state, and having superior safety and stability; an external composition for skin formulating said antiwrinkle agent; a lipolysis promoter that is effective in improving an obese constitution by promoting a reduction of systemic or local adipose tissue, or inhibiting or preventing obesity by preventing increases in adipose tissue, while also suppressing pungency and aromas that impair likeability; and, an external composition for skin and food and beverage composition formulating said lipolysis inhibitor, are provided.

The invention claimed is:

1. A method for promoting lipolysis, comprising applying to skin a composition comprising an effective amount of an active ingredient chosen from compounds of formula (1):

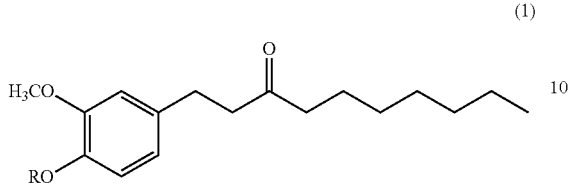

(1)

wherein R represents a hydrogen atom or an acyl group having from 2 to 20 carbon atoms.

2. The method according to claim 1, wherein R is a hydrogen atom.

3. The method according to claim 1, wherein the active ingredient is an extract obtained from guinea ginger and/or an acylation treatment product of said extract.

4. A method for promoting lipolysis, comprising eating or drinking a food or beverage composition comprising an effective amount of an active ingredient chosen from compounds of formula (1):

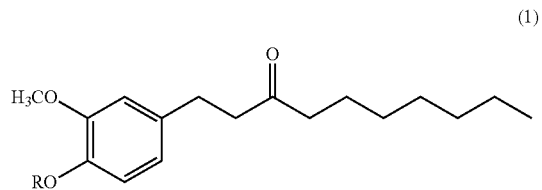

(1)

wherein R represents a hydrogen atom or an acyl group having from 2 to 20 carbon atoms.

5. The method according to claim 4, wherein R is a hydrogen atom.

6. The method according to claim 4, wherein the active ingredient is an extract obtained from guinea ginger and/or an acylation treatment products of said extract.

* * * * *